(12) United States Patent
Macdonald et al.

(10) Patent No.: US 9,555,192 B2
(45) Date of Patent: Jan. 31, 2017

(54) DRUG DELIVERY DEVICE, ASSEMBLY FOR A DRUG DELIVERY DEVICE AND METHOD FOR SETTING UP A DRUG DELIVERY DEVICE

(75) Inventors: Catherine Anne Macdonald, Ashby-de-la-Zouch (GB); Robert Veasey, Leamington Spa (GB); Garen Kouyoumjian, Leamington Spa (GB); Christopher Jones, Tewkesbury (GB); Alexander Ian Bailey, Peasmarsh (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1270 days.

(21) Appl. No.: 13/497,376

(22) PCT Filed: Sep. 29, 2010

(86) PCT No.: PCT/EP2010/064410
§ 371 (c)(1),
(2), (4) Date: Oct. 17, 2012

(87) PCT Pub. No.: WO2011/039219
PCT Pub. Date: Apr. 7, 2011

(65) Prior Publication Data
US 2013/0030409 A1 Jan. 31, 2013

(30) Foreign Application Priority Data
Sep. 30, 2009 (EP) .................................... 09171751

(51) Int. Cl.
*A61M 5/00* (2006.01)
*A61M 5/24* (2006.01)
(Continued)

(52) U.S. Cl.
CPC .............. *A61M 5/24* (2013.01); *A61M 5/3146* (2013.01); *A61M 5/31571* (2013.01);
(Continued)

(58) Field of Classification Search
CPC .. A61M 5/24; A61M 5/31551; A61M 5/3158; A61M 5/31585; A61M 5/31535; A61M 5/31575
(Continued)

(56) References Cited

U.S. PATENT DOCUMENTS

| 4,973,318 A | 11/1990 | Holm et al. |
| 5,279,585 A * | 1/1994 | Balkwill ............. A61M 5/3158 222/309 |
| 2009/0264828 A1 | 10/2009 | Dette et al. |

FOREIGN PATENT DOCUMENTS

| WO | 2004/089540 | 10/2004 |
| WO | 2006/024461 | 3/2006 |

(Continued)

OTHER PUBLICATIONS

International Search Report for International App. No. PCT/EP2010/064410, completed Jun. 10, 2011.
(Continued)

*Primary Examiner* — Phillip Gray
(74) *Attorney, Agent, or Firm* — McDonnell Boehnen Hulbert & Berghoff LLP (57) ABSTRACT

The instant application is directed to an assembly for a drug delivery device which is arranged to operate in two distinct modes, a priming mode starting from a pre-priming state and a dispense mode operating in a post-priming state, and a drug delivery device comprising this assembly. The assembly comprises a dose member, an actuating member and a piston rod which is configured to act on a bung of an assembled cartridge containing the drug. In the pre-priming state the actuating member is configured to be moved by a user such that the movement of the actuating member causes a movement of the dose member and such that the movement of the dose member causes a movement of the piston rod. In the post-priming state the dose member is configured to be moved by a user without causing a movement of the actuating member in order to perform a set and dispense action of the drug delivery device.

13 Claims, 4 Drawing Sheets

(51) Int. Cl.
    *A61M 5/31*      (2006.01)
    *A61M 5/315*     (2006.01)
    *A61M 5/20*      (2006.01)

(52) U.S. Cl.
    CPC ....... *A61M 5/31578* (2013.01); *A61M 5/2448* (2013.01); *A61M 2005/2073* (2013.01); *A61M 2005/2451* (2013.01)

(58) Field of Classification Search
    USPC .................................................. 604/207, 211
    See application file for complete search history.

(56) References Cited

FOREIGN PATENT DOCUMENTS

| WO | 2007/107431 | 9/2007 |
|---|---|---|
| WO | 2008/087071 | 7/2008 |
| WO | 2009/007229 | 1/2009 |
| WO | 2009/097934 | 8/2009 |
| WO | 2006/037434 | 4/2013 |

OTHER PUBLICATIONS

European Office Action for EP Application No. 10760371.7, dated Nov. 11, 2015.

\* cited by examiner

DRUG DELIVERY DEVICE, ASSEMBLY FOR A DRUG DELIVERY DEVICE AND METHOD FOR SETTING UP A DRUG DELIVERY DEVICE

CROSS REFERENCE TO RELATED APPLICATIONS

The present application is a U.S. National Phase Application pursuant to 35 U.S.C. §371 of International Application No. PCT/EP2010/064410 filed Sep. 29, 2010, which claims priority to European Patent Application No. 09171751.2 filed on Sep. 30, 2009. The entire disclosure contents of these applications are herewith incorporated by reference into the present application.

FIELD OF INVENTION

The present invention relates to an assembly for a drug delivery device being configured to operate in two distinct modes, a priming mode and a dispense mode and further relates to a drug delivery device comprising this assembly. The invention further relates to a method for setting up a drug delivery device, particularly afore said drug delivery device.

BACKGROUND

Drug delivery devices are generally known to be used for the administration of medicinal products, particularly fluid medicaments, for example insulin or heparin, but also for other medicinal products for self-administration by a patient. Often, drug delivery devices are pen-type injectors which dispense a pre-set dose of a fluid medicinal product.

Prior to the first use of a drug delivery device, the drug delivery device usually has to be primed. During a priming-step gaps which are contained in the drug delivery device between components may be closed, particularly gaps between components which are involved in the mechanism for dispense of the drug contained in the drug delivery device (for example a gap between a piston rod and a cartridge bung). These gaps may be a consequence of the tolerances associated with all the assembled parts which may occur through the manufacturing of the device and the requirement not to preload the bung axially in the assembled device. Usually, all gaps between components being involved in the mechanism of the drug delivery device are closed, particularly the gap between the piston rod and the cartridge bung. However, in certain embodiments reducing the gaps to a certain extent may also be possible. After having performed the priming-step, the device is in a primed condition so that the user can now dispense the intended dose exactly, including the first dispensed dose.

A problem of such drug delivery devices is that the users of the drug delivery device who are not familiar with such devices may fail to or incorrectly prime the device before dispensing the first dose. If this occurs, the user may inject the prime fluid or the correct volume of medicament may not be delivered in the first dose. In particular, often the user does not know whether he has primed the device before an intended injection of a dose. Usually, the unfamiliar user cannot see if he has to perform a priming-step before using the device in the correct way.

SUMMARY

It is an object of the present disclosure to provide an assembly for the use in a drug delivery device which is more user friendly.

This objective may be achieved by the subject matter of the independent claims. Further features are the subject matter of dependent claims and of the description.

According to a first aspect, an assembly for a drug delivery device is provided. The assembly is arranged to operate in two distinct modes, a priming mode starting from a pre-priming state and a dispense mode operating in a post-priming state. The assembly has a distal end and a proximal end, which are spaced apart in the direction of an axis. The assembly according to this aspect comprises a dose member, an actuating member and a piston rod which is configured to act on a cartridge bung retained in an assembled cartridge which contains the drug. In the pre-priming state, the actuating member is configured to be moved by a user such that the movement of the actuating member causes a movement of the dose member; this movement of the dose member further causes a movement of the piston rod. In the post-priming state the dose member is configured to be moved by a user without causing a movement of the actuating member by moving the dose member, particularly in order to perform a set and dispense action of the drug delivery device.

The assembly according to the instant invention and the components being involved in the priming mechanism and the set and dispense mechanism, respectively, allow a differentiated action to be performed by the user in the priming-step compared with the action to be performed in the dispense mode. Therefore, the attention of the user is drawn to the need to prime the drug delivery device and the user is forced to prime the device through a recognizable different action before set and dispense of a dose. This mitigates the risk associated with the priming-step by discouraging the user from injecting the prime fluid and distinguishing the prime fluid from the doses of medicament intended for the patient. Particularly, the alternative operation required to prime is intentionally difficult to undertake while the device is inserted in the body as e.g. a two-handed operation would be required. Upon determining whether the dose member is moveable, particularly moveable in the direction of the axis between the distal and the proximal end of the device, without moving the actuation member, the user can easily decide whether the drug delivery device is in a primed or not primed state.

The "priming mode" according to the instant invention shall mean the mode during which the priming-step is carried out. Usually, during the priming mode no set and dispense action is possible. The priming mode starts from a pre-priming state and usually ends at a post-priming state. At the end of the priming mode (i.e. in the post-priming state) the assembly or drug delivery device has been brought into a mode where the priming-step has been finished and where a set and dispense action may be carried out.

Accordingly, the term "dispense mode" according to the instant invention shall mean the mode which usually follows directly on the priming mode, i.e. the dispense mode operates in a post-priming state.

The "distal end" of the device or component or assembly of the device shall mean the end, which is closest to the dispensing end of the device. The "proximal end" of the device or assembly or component of the device shall mean the end, which is furthest away from the dispensing end of the device.

The "axis" according to the instant invention shall mean the axis being defined by a point at the proximal and a point at the distal end. These points may, for example, be the center of the proximal face of the dose member and the center of the distal face of the cartridge, particularly the distal face of the cartridge part comprising a screw thread for securing a needle assembly. Particularly and in more detail the axis extends from the proximal end to the distal end through the device or assembly so that the intersection point of the axis and a perpendicular intersection plane of the device or assembly is located in the geometric center of the intersection plane or close to this center.

The term "dose member" according to the instant invention shall mean any component designed to be operated by a user in the dispense mode and preferably to cause an axial movement (i.e. a movement along aforesaid axis in proximal or distal direction) of components within the drug delivery device giving rise to a set and dispense action.

The term "actuating member" according to the instant invention shall preferably mean a component which is substantially or exclusively used during the priming mode and is usually not involved in the set and dispense action during the dispense mode. Usually, the actuating member will be operated by the user in order to start the priming-step. The actuating member may be of unitary or multipart construction and may be completely or partially visible for the user in the pre-priming state and the priming mode and usually also in the dispense mode. The actuating member may be arranged in the area where the axis (between the distal end and the proximal end) extends, i.e. in the medial part (center) of the assembly or the drug delivery device. Alternatively, the actuating member may be arranged at the outer surface of the drug delivery device or assembly, i.e. the lateral part, and may also be arranged between both foresaid positions, i.e. in an intermediate position. The actuating member may cover the proximal end of the assembly or drug delivery device completely. However, usually the proximal face of the dose member will be visible for the user not only in the dispense mode but also in the pre-priming state and the priming mode. In most embodiments, the proximal end of the dose member even is identical with the proximal end of the drug delivery device. In order to facilitate the movement of the actuating member, the visible surface of the actuating member in the pre-priming state may contain grip elements, for example a structured surface. These grip elements may or may not be visible during the dispense mode. If those grip elements are concealed during the dispense mode, particularly if the actuation member is arranged in a medial or intermediate position within the drug delivery device, the user can easily realize that the priming-step has been carried out already. Further, a misalignment of the grip elements, for example with respect to corresponding elements arranged on the body or any other component of the housing, can be used as an indicator that the priming-step has not yet been carried out.

The term "piston rod" according to the instant invention shall mean a component designed to translate movements, particularly axial movements, through the drug delivery device. Preferably the piston rod translates movements from the dose member to the bung retained in the cartridge, for the purpose of dispensing an injectable product, particularly a fluid medicinal product. Usually, the piston rod also translates movements for the purpose of dispensing priming-fluid. The movement of the piston rod may be a movement in axial direction only (i.e. a movement in the direction of the axis defined before); however, the movement of the piston rod in axial direction may also involve a rotation of the piston rod around its longitudinal axis. The piston rod may be flexible or not, may be a simple rod, a lead screw, a rack and pinion system, a worm gear system, or the like. The piston rod may have a circular or non-circular cross-section. It may be made of any suitable material known by a person skilled in the art and may be of unitary or multipart construction. In an embodiment, the piston rod comprises a series of one or more sets of longitudinally spaced ribs and/or indentations.

The cartridge contained in the assembly or drug delivery device holds a number of doses of the medicinal product to be dispensed. The cartridge retains a bung; upon movement of the piston rod in distal direction the piston rod usually bears against the bung and causes dispensing of a dose of the drug.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

According to an embodiment, in the pre-priming state the actuating member is engaged with the dose member by first engagement means. The first engagement means are arranged such that the dose member and the actuating member are disengaged by the movement of the actuating member (during the priming mode).

The first engagement means are usually arranged in a way that the direction of movement of the actuating member with respect to the dose member during the priming-step is different to the direction of movement of the dose member during the set and dispense action. If, for example, the movement of the dose member during the set and dispense action is a movement in direction of the axis, the movement of the actuating member with respect to the dose member during the priming-step also involves a rotation of the actuating member around the axis or is a rotation around the axis exclusively. If the dose member is exclusively rotated during the dispense mode in order to set and dispense a drug, the movement of the actuating member with respect to the dose member during the priming-step involves a movement in the direction of the axis or is exclusively a movement in the direction of the axis.

The engagement means according to this embodiment usually are configured to directly cause a movement of the dose member upon moving the actuating member. In other words, the dose member and the actuating member are configured in a way that—if the movement of the dose member during the priming-step is a movement in direction of the axis—the engagement means cause a movement of the dose member and the actuating member in direction of the axis and additionally cause a rotation of the actuating member around the axis but no rotation of the dose member; therefore, the first engagement means are configured so that the actuating member and the dose member "travel together for some time"—in the example before in the direction of the axis—before the disengagement of actuating member and dose member takes place. Therefore, usually the first engagement means are (or alternatively the combination of the first engagement means and the second engagement means, described below, is) configured to cause a co-movement of dose member and actuating member in a first direction and a movement of the actuating member only in a second direction, wherein the engagement means are further configured so that only upon moving the actuating member in the second direction for a certain distance a disengagement of actuating member and dose member is possible.

The first engagement means may involve a groove in the surface of the actuating member facing the dose member or a groove in the surface of the dose member facing the actuating member. The corresponding part may contain a bar or a pivot or something similar in order to interact with the groove. However, the first engagement means are not restricted to a surface element being a groove or a similar element and an element of the corresponding part gearing into this groove or groove-like element, the first engagement means may also involve a rabbet on the facing surfaces of the actuating member and the dose member, or also a guidance element being not located at the facing surfaces of that members or the like.

In an embodiment being alternative to the embodiment described before, the dose member is fixed to the actuating member in any direction of movement in the pre-priming state. Therefore, at the beginning of the priming-step the movement of the actuating member causes a movement of the dose member in exactly the same direction, i.e. if the movement involves a rotation and a movement in distal axial direction both members, the actuation member and the dose member, perform this movement; if the movement is a movement in distal axial direction only both elements perform a movement in distal axial direction only. Then, during the priming-step, a mechanism is started which releases the actuating member from the dose member upon which in a later set and dispense action the dose member is moveable in direction of the axis without moving the actuating member in this direction.

In an embodiment, the mechanism described in the paragraph before involves interconnection means fixing the actuating member to the dose member. Usually, these interconnection means extend in a spatial direction being different from the direction of the axis. During the priming-step a force is exerted on these interconnection means (which may for example be a cotter pin, a bolt or something similar) upon which the engagement of the interconnection means with at least one of the actuating member and the dose member is released and upon which the dose member and the actuating member are disengaged and whereupon the dose member is movable independent from the actuating member. The force may for example result from a component of the drug delivery device being arranged in a way that upon movement of the actuating member (and the dose member), for example a movement in the direction of the axis, this component approximates and subsequently contacts the interconnection means and eventually exerts a force from on the interconnection means resulting in a movement of the interconnection means and a disengagement of the actuating member and the dose member. The part of the component being responsible for exerting the force may comprise a bulge. Said component may for example be the body comprised in the drug delivery device, it may be an internal part of the drug delivery device, particularly being arranged in the medial or intermediate part of the device, for example a drive feature or a part of the piston rod, and it may also be a component which is designed to fulfill the purpose of exerting the force only and is not involved in the mechanism to set and dispense a dose of the drug.

The assembly of the present invention may further comprise a body (as already mentioned in the paragraph before). According to a further embodiment of the present invention the actuating member adjoins this body and is moveable with respect to the body in the pre-priming state.

Usually, the actuating member is fixed to the body during the dispense mode or at least engaged with the body during the dispense mode in a way that the actuating member is moveable with respect to the body only in a direction which is different from the direction of movement of the dose member performed during a set and dispense action. In most embodiments, the dose member will be moved in distal and proximal direction with respect to the axis during the set and dispense action and, therefore, the actuating member is fixed to the body at least in the direction of the axis then but may perform a rotation around the axis.

In order to enable a fixing of the actuating member to the body at least in one direction, the body and the actuating member may contain second engagement means the shape of which may be configured as described before for the first engagement means. However, the second engagement means may also be configured to allow a latching of the actuating member and the body during or at the end of the priming-step. However, also separate latching means which fulfill the purpose described before may also be present beside the second engagement means.

In an embodiment, the second engagement means are configured to force the actuating member to perform the specific movement which is visible for the user during the priming-step. As mentioned before, this movement of the actuating member with respect to the body is usually different to the movement of the actuating member with respect to the dose member. Therefore, according to this embodiment, the second engagement means are responsible for causing a movement of the actuating member which also results in a movement of the internal parts of the drug delivery device causing the dispense of priming liquid in the end. Usually, these second engagement means are also responsible for the movement of the actuating member in a different direction compared to the movement which causes the dispense of priming liquid, being a movement in a direction which results in a disengagement of the first engagement means and the release of the dose member with respect to the actuating member.

The second engagement means may, for example, be configured to allow a rotation or a helical movement of the actuating member with respect to the body in the pre-priming state or during the priming mode, at least at the beginning of the priming-step. However, if the movement of the dose member causing the dispense of prime liquid is a rotation around the axis, the second engagement means may also be provided to allow a movement of the actuating member with respect to the body in the direction of the axis only.

According to a further embodiment, the assembly of the instant invention further comprises a drive feature. The drive feature is provided to cause a movement of the piston rod, particularly a movement in distal direction. The drive feature is configured such that in the pre-priming state or during the priming-step a movement of the actuating member (which usually acts on the dose member which in turn acts on the drive feature) causes a movement of the drive feature. The drive feature is further configured such that in the post-priming state the drive feature is coupled to the dose member, i.e. that any movement of the dose member by the user in order to carry out a set and dispense action causes a movement of the drive feature.

The term "drive feature" according to the instant invention shall mean any component adapted to operate through/within the housing of the drug delivery device and is designed to translate an axial movement or sometimes also a rotation through/within the drug delivery device, preferably from the dose member to the piston rod or during the priming-step also from the actuating member to the piston rod. The drive feature may be of unitary or multipart construction. In an embodiment, the drive feature is releasably engaged with the piston rod, i.e. the drive feature and the piston rod interact in a way that a force or movement is translated in one direction only.

In an embodiment, the drive feature may contain at least one rack, i.e. a component having a linear array of ribs or indentations or gear-formed teeth or mixtures of afore said features. The drug delivery device may contain a further rack not located in the drive feature and corresponding to the rack located in the drive feature; this further rack, the rack in the drive feature or both are flexible or moveable in one or more directions, usually one direction. However, the further rack is usually fixed to the body of the drug delivery device or another component of the housing of the drug delivery device, and is then at least a part of the inner housing.

The term "housing" according to the instant invention shall preferably mean any housing having a unidirectional axial coupling to prevent a proximal movement of specific components of the drug delivery device. The housing may be designed to enable the safe, correct and comfortable handling of the drug delivery device or any components of its mechanism. Usually, it is designed to house, fix, protect, guide any of the components by limiting the exposure to contaminants, such as liquid, dust, dirt etc. Further it may be designed to be engaged with any of the components of the drug delivery device. The housing may be of unitary or multipart construction. The body as described before is a component of the housing; a further components may be a cartridge holder; also the actuating member is usually a component of the housing, if the actuating member is arranged in the lateral part of the drug delivery device.

According to this embodiment, the drive feature is usually fixed with respect to the dose member at least in one direction of movement, particularly the direction of the movement of the dose member during the set action. The drive feature may also be fixed to the dose member in any direction of movement during the dispense mode.

In the pre-priming state, the drive feature is configured such that a movement of the actuating member is translated to a movement of the drive feature. This may be due to an interaction of the drive feature and the dose member as outlined above; however, also a direct interaction of the drive feature and the actuating member may be possible in specific embodiments.

In order to allow an interaction of the drive feature and the dose member or a fixing of the drive feature to the dose member, third engagement means may be provided. For example, the engagement means may involve a bulge on one of the surfaces of the dose member and the drive feature facing each other and a detent on the surface of the other component. If the drive feature interacts with the actuating member, the facing surfaces of these two components may be configured accordingly. Usually during the priming-step, by performing a movement with respect to the drive member, for example a movement in proximal direction, the dose member will be fixed to the drive feature by the third engagement means. For example, two corresponding parts of the third engagement means may interact in a way that the inverse movement of the dose member with respect to the drive member is not possible anymore.

In a further embodiment, the assembly according to the instant invention further comprises a resilient element. The resilient element is engaged with the dose member and is usually in a compressed state in the pre-priming state and usually in a non-compressed state in the post-priming state. The resilient element is configured to cause the dose member to protrude with respect to the actuating member when the dose member and the actuating member are disengaged during the movement of the actuating member in the priming-step.

"Resilient element" according to the instant invention shall preferably mean an element which may be in different states of matter, a compressed state and a extended state, and may further be an element being able to exert a force on the adjacent components of the assembly at least either in the compressed state or in the extended state, particularly being able to exert a force on the adjoining components being arranged in the direction of the axis. The resilient element may be made of any material, particularly of any metallic material. The resilient element may be a spring, for example a helical spring and a spring similar to a cantilever spring or leaf spring; the resilient element may also involve an elastomeric compound which allows to store energy in the extended state which can be used to let the dose member protrude with respect to the actuating member.

Usually, the resilient element is arranged in the medial part of the assembly, or in an intermediate part. Particularly, the resilient element may be arranged completely or partially inside the dose member, i.e. it may extend from the inner surface of the proximal end of the dose member to the distal end of the dose member. The resilient element usually is arranged directly between the dose member and the drive feature; however, also arrangements between other components may be possible for example an arrangement between the body and the dose member is possible. Usually, the resilient element will also exert the force in the pre-priming state on the dose member and the drive feature or the body, respectively. The resilient element may be just one part; it may also be a multipart component for example an assembly of two or more springs in the shape of a leaf spring.

According to the instant invention, the arrangement of a resilient element inside the assembly enables an easy way to make the primed drug delivery device distinguishable from an unprimed drug delivery device. As the dose member protrudes from the actuating member during the priming-step, the user can easily distinguish a primed and a not primed device and knows that a set and dispense action may be performed by operating the protruded dose member. If the actuating member is partially covered by the dose member in the pre-priming state, the actuating member may even "disappear" for the user after expansion of the resilient element.

In an embodiment, the resilient element does not change its state of matter anymore as soon as the priming-step is performed, i.e. the resilient element is not compressed or expanded during the set and dispense action. However, additional embodiments, wherein the resilient element is involved in the movement of the dose member during the set and dispense mode are possible. An additional embodiment may, for example, be the 'push-push' embodiment where the resilient element itself undertakes the setting operation and the user merely dispenses by pushing the button. Once the button is released, the force exerted by the resilient element, for example the spring, pushes the button back out, setting the next dose.

According to a further embodiment, the present invention, the dose member comprises an actuation area in its lateral part. This actuation area may be used during the set and dispense actions in order to move the dose member (and thereby effecting the delivery of a dose of the drug).

The actuation area may comprise for example grooves or ribs for a better handling and may additionally or alternatively be formed in a way which simplifies carrying out the movement of the dose member during the set and dispense action, for example a dent-like structure having the size of a fingertip.

In an embodiment, the actuation area is at least partially covered by a component of the assembly in the pre-priming step. Usually, the actuation area is not covered by any component of the assembly in the dispense mode. Therefore, the user of the drug delivery device will immediately realize that he may not carry out a set and dispense action as he cannot see the whole actuation area or—if the actuation area is fully covered—cannot see the actuation area at all in the pre-priming state. According to some embodiments, the whole lateral surface of the dose member may not be visible for the user in the pre-priming state.

According to a further embodiment, of the present invention, the actuating member is a sleeve. If a sleeve is used as an actuating member, the priming-mechanism of the present invention may easily applied to any known drug delivery device; the sleeve may be arranged on the surface of the existing drug delivery device without changing the design and the mechanism of this existing drug delivery device substantially. Basically, usually just engagement means and—if necessary—the interconnection means described before have to be arranged on the surfaces of the sleeve and the other components interacting with the sleeve.

The sleeve may be a one part component but also a multipart component; it may contain openings or transparent parts; it may also be fabricated without any area making visible the adjoining component underneath the sleeve. If openings or transparent parts are contained, the assembly or drug delivery device may be configured in a way that the user gets information from the surface of the adjoining component underneath the sleeve, the information being different in the pre-priming state and the dispense mode or not existent in one of these states or modes. For example, the user may see an information that he has to prime the device in the pre-priming state and may see an information through the same or a different opening that the drug delivery device is in the dispense mode now.

According to a further embodiment, the information described before may also be arranged on a component, particularly the surface of the body which is not covered at all by the sleeve (or the actuating member in general) in the pre-priming state and which is covered during the dispense mode. For example, arrows showing the direction of movement to be carried out during the priming-step may be arranged on this surface not being covered by the actuating member. The drug delivery device may also contain information that the device is in an unprimed state as long as arrows or information is visible in this area.

According to a further embodiment, the assembly according to the instant invention is configured so that the dose member is moveable in proximal direction of the axis in order to allow setting of a dose of a drug during the dispense mode. Furthermore, according to this embodiment, the dose member is moveable in distal direction of the axis after having carried out the setting of a drug in order to allow a dispense of the dose.

Usually, the assembly or drug delivery device is configured so that either movement in proximal direction or a movement in distal direction is possible during the set action and that only a movement in the inverse direction is possible during the dispense action.

According to a further aspect, a drug delivery device comprising an assembly as described before is provided.

The drug delivery device may be an injection device. The drug delivery device may be a pen-type device, e.g. a pen-type injector which may be an injector for single-use or multiple-use. The cartridge may hold a plurality of doses of a drug. Preferably, the drug comprises a liquid medication, such as a long-acting or short-acting insulin, GLP-1, heparin or growth hormones. The drug delivery device may be designed such that it may accommodate cartridges of different sizes. Additionally or alternatively, the drug delivery device may be designed such that it may accommodate cartridges of different shapes.

The cartridge or the cartridge holder may be permanently secured to the body by connection means. For example, the connection means may be joined by welding. Additionally or alternatively, the connection may comprise use of a separate connecting material such as an adhesive. The cartridge holder may be reversibly or irreversibly secured to the body, alternatively, the cartridge may be directly secured to the body and the use of a cartridge holder may be redundant.

In an embodiment the drug delivery device is a fixed dose device. This means that the device always dispenses a pre-given, non-user-variable, e.g. constant or variable dose of drug. Therefore, the drug delivery device may, for example, be used for drugs which should always be administrated by the user in the same dose. Especially if the drug should always be dispensed in a fixed dose, it is expedient that the first dose has exactly the same volume as the following doses and that the priming step is carried out correctly. In one embodiment the device is a pen-type injector.

The drug delivery device may be used with a pen injector for the delivery of doses from a cartridge into the body by means of a needle. The injector-pen may be a disposable pen, for example a disposable fixed-dose injector. However, the present invention is not limited to disposable fixed-dose injectors; also, variable dose pens and reusable devices are possible.

According to a third aspect, a method for setting up a drug delivery device is provided.

The method comprises the following steps:

A) A drug delivery device is provided which has a distal end and a proximal end, wherein the distal end and the proximal end are spaced apart in the direction of an axis. Further, the provided drug delivery device comprises a dose member, an actuating member which is initially coupled with the dose member and a cartridge holding at least one dose of a drug. In step B) the actuating member is moved upon which priming liquid is dispensed and a disengagement of the actuation member and the dose member is caused. In particular, the drug delivery device according to the third aspect of the instant invention is a drug delivery device as described before and comprises an assembly as disclosed in the preceding part of the description.

Of course, features relating to different aspects described above may be combined with each other. Further features, advantages and expediencies become apparent from the following description of the exemplary embodiments in conjunction with the accompanying drawings.

BRIEF DESCRIPTION OF THE FIGURES

Elements of the same kind and identically acting elements may be provided with the same reference numerals in the figures.

DETAILED DESCRIPTION

Figure 1A:
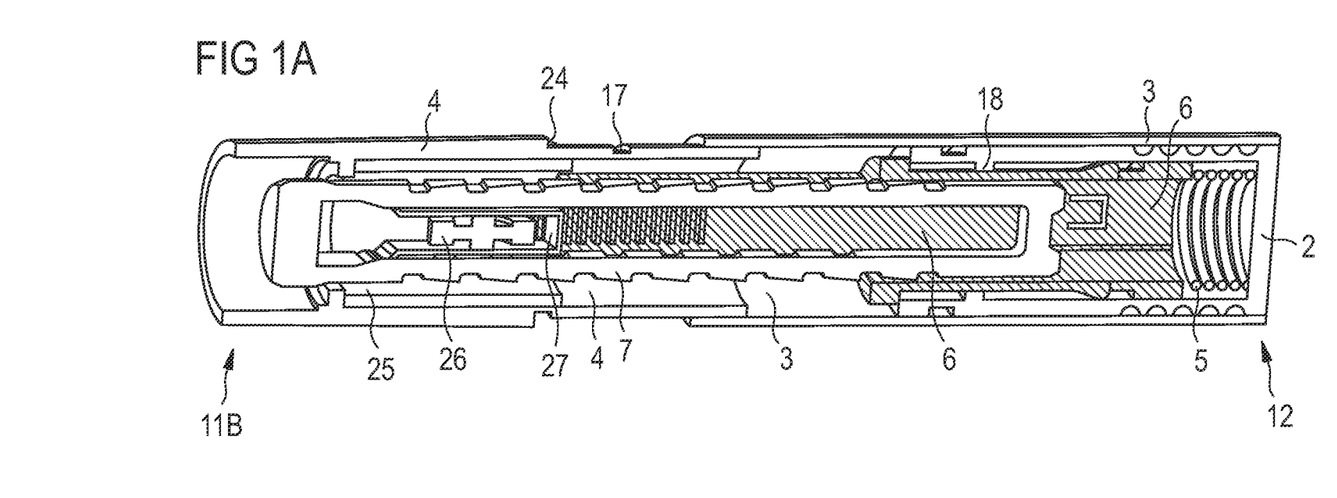
FIG. 1A shows a cross-section of an assembly of a drug delivery device.

In FIG. 1A, an assembly for a drug delivery device is shown. The assembly comprises a body 4 and an actuating member 3 in the shape of a sleeve adjoining the body 4. The housing of a drug delivery device comprising an assembly according to this embodiment comprises three main parts: the body 4, the actuating member 3 and a cartridge holder 14 (not shown). The assembly has a distal end 11B and a proximal end 12. At the proximal end 12, the dose member 2 is arranged. The lateral part of the dose member 2 is fully covered by the actuating member 3. At the proximal face of the assembly, however, substantially the proximal part of the dose member 2 is visible. The outer surface of the body comprises two major areas, the area being covered by the actuating member in the dispense mode extending from the proximal end of the body 4 (located in the middle of the figure) to the flange feature 24. The part of the body 4 extending from the flange feature 24 to the distal end of the body 11B is also visible for the user during the dispense mode unless the cartridge holder 14 is imposed on the lateral part of the distal end 11B of the body 4 during assembly of the drug delivery device.

During the priming-step, the actuating member 3 is moved towards the flange feature 24 until no further movement in distal direction is possible. As a guidance element for this movement the slot 17 is used which is a part of the second engagement means 16 (not shown completely). The dose member 2 comprises third engagement means 18 being configured to fix the dose member to the driving feature 6 (shown as hatched area(s)) after having performed the priming-step. Inside the dose member a resilient element 5 (in the form of a helical spring) is located. Adjoining to the proximal end of the spring, the proximal part of the dose member is located. Adjoining to the distal end of the spring, the proximal part of the driving feature 6 is located. The driving feature 6 extends from the distal part of the resilient element 5 to the gear 26. In the distal area of the drive feature ribs and indentations are visible (they are visible through a channel within the piston rod 7 being arranged in order to interact with the gear 26). The gear 26 comprises additionally a carrier 27. The assembly further comprises an internal housing 25, being for example a fixed rack.

In general, according to the instant invention, gear shall mean a component to transmit a force or a motion, for example a toothed wheel used in conjunction with a rack or another gear or both. In the present embodiment the gear is a spur-gear mounted within the carrier 27.

Figure 1B:
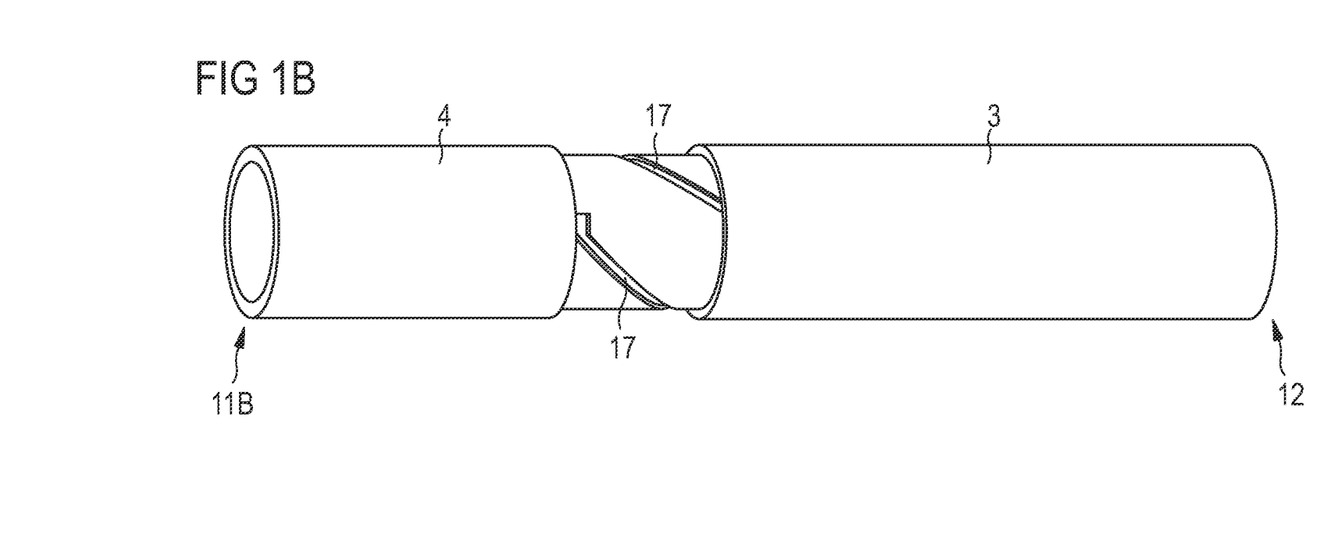
FIG. 1B shows an external view on the assembly of FIG. 1A.

FIG. 1B shows the external view of the assembly of FIG. 1A. The assembly is shown in an unprimed state. Therefore, the area of the body 4 being covered by the actuating member 3 later on is visible. In this area the slot 17 serving as a guidance element for the movement of the actuating member 3 in distal direction during the priming-step is located (the slot 17 is a part of the second engagement means 16, which are not shown completely). This slot 17 or channel is located in a helical manner on the surface of this part of the body 4 to be covered by the actuating member 3 in order to allow a helical movement of the actuating member with respect to the body during the priming-step.

Figure 2A:
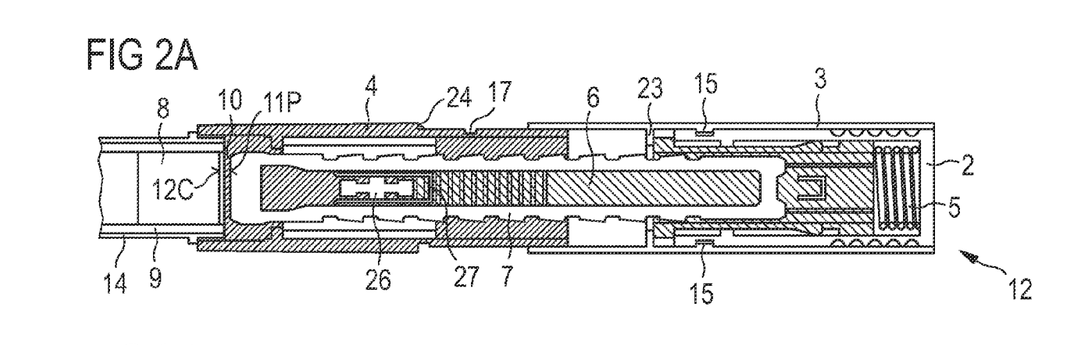
FIGS. 2A to 2C show a cross-section of a partial view of a drug delivery device containing the assembly of FIG. 1A in the pre-priming state (FIG. 2A), during the priming mode (FIG. 2B) and in a post-priming state (FIG. 2C).
Figure 2B:
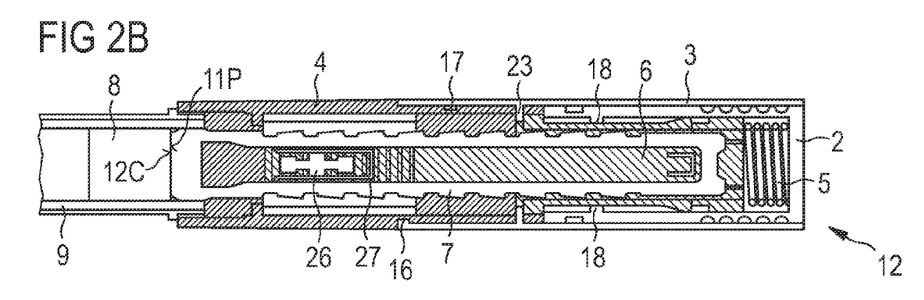
Figure 2C:
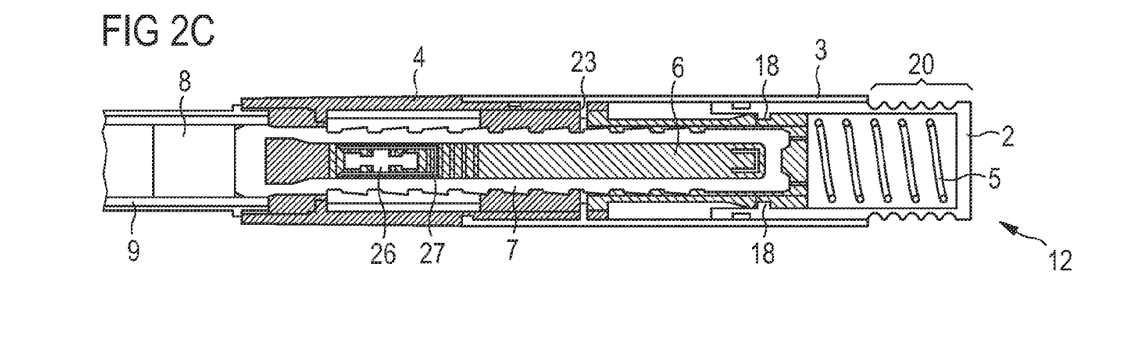

FIGS. 2A to 2C show cross-sections of a drug delivery device before, during and after priming. In all figures, the distal part of the drug delivery device is omitted for the sake of clarity.

In FIG. 2A, compared to FIG. 1A, a cartridge holder 14 containing the cartridge 9 retaining the bung 8 is assembled to the assembly of FIG. 1A. Between the proximal face 12C of the bung and the distal face 11P of the piston rod 7 a gap 10 can be seen, which is a consequence of the tolerances associated with all the assembled parts and the requirement not to pre-load the bung axially during assembly of the device. When the drug delivery device is in the pre-priming state, the drive feature 6 (shown as hatched area(s)), having the form of a moving rack, is located in its position furthest in the proximal direction relative to the internal housing 25. The housing is in this embodiment a fixed rack having gears and indentations on opposite side of the (spur-)gear 26 with respect to the moving rack (drive feature 6). Usually, a prime stroke being smaller than the dose dispense stroke is intended; therefore the drive feature being a moving rack may be assembled in a pro-rata proximal position relative to the fixed rack (internal housing 25) some of the way through its travel from its position furthest towards the distal direction relative to the fixed rack. The dose member 2 is constrained to the drive feature 6 such that it cannot rotate but can move axially relative to the drive feature 6 for example due to a splined engagement. The dose member 2 is constrained by first engagement means 15, for example a lug in a channel so that it cannot move axially relative to the actuating member 3 until the priming-step has at least partially been carried out; usually the dose member 2 is constrained until after the prime fluid has been dispensed. In the pre-priming state, the dose member 2 does not protrude from the actuating member 3 inhibiting access by the user. The drive feature 6 is constrained by a shelf 23, particularly on the inner surface of the actuating member 3 such that it cannot initially move in the distal direction relative to the actuating member 3. The resilient element 5, being a helical spring is compressed between the proximal end of the drive feature 6 and the inner surface of the proximal end of the dose member 2. The actuating member 3 is in its position furthest in the proximal direction relative to the body 4 (shown as differently hatched area(s) compared to the driving feature 6) and is preferably held in position by a detent feature (not shown) between the actuating member 3 and the body 4 to prevent rattling of the mechanism before use and help prevent accidental priming. It is also desirable to keep the actuating member 3 in the correct pre-prime orientation so that any additional indicators are aligned for the user to see. Actuating member 3 is constrained by second engagement means 16 (not shown completely) to move through a channel 17 in the body 4. Relative to the dose member 2 the actuating member 3 can rotate and any movement of the actuating member 3 in distal direction will result in a movement of the dose member in axial direction being followed by a movement of the driving feature 6 in distal direction and via translation of the movement by the gear 26 the movement of the piston rod 7 in distal direction (resulting in the dispense of priming liquid). Finally, the actuating member 3 may rigidly and permanently lock to the body 4, for example by means of a clip feature (not shown).

To prime the device, the user simultaneously twists and pushes the actuating member 3 towards the body 4 to allow the actuating member 3 to screw onto the body 4 along the helical channel 17 ending up in a position where the distal end of the actuating member 3 abuts the flange feature 24 shown in FIG. 2A. FIG. 2B shows the situation after the distal end of the actuating member 3 abuts the flange feature 24 of the body 4. The dose member 2 traveled axially together with the actuating member 3 in the distal direction but did not rotate with it, relative to the body 4. The shelf 23 may serve as a component fixing the actuating member 3 to the body 4 in any direction of movement. The distal face of the dose member 2 drives the drive feature 6 in the distal direction advancing the main drive mechanism to deliver the prime fluid. The gap 10 being present in FIG. 2A disappeared and the distal end 11P of the piston rod 7 abuts the proximal end 12C of the bung 8, in FIG. 2B with respect to FIG. 2A also the bung 8 moved forward slightly in addition to the gap 10 being taken up. The situation in FIG. 2B shows the resilient element 5, i.e. the spring, still in the compressed state of matter and shows the dose member 2 and the actuating member 3 relative to each other in the position where already the disengagement of the actuating member 3 and the dose member started to take place.

As the dose member 2 and the actuating member 3 have a new orientation relative to each other the dose member 2 and the actuating member 3 are disengaged and the first engagement means 15 (which are only visible in FIG. 2A but not in FIG. 2B anymore) do not cause restraining of the dose member 2 to the actuating member 3 any longer. Due to this engagement, the actuating member 3 no longer prevents the dose member 2 from moving axially in the proximal direction relative to the actuating member 3. The resilient element 5 extends and pushes the dose member 2 in the proximal direction such that the dose member 2 now protrudes from the actuating member 3. The third engagement means 18 located on the dose member 2, e.g. the lug on the dose member 2, slides over the corresponding part(s) arranged on the drive feature 6 (for reason of clarity the corresponding part(s) arranged on the drive feature are not labeled with "18" in all figures), being for example detents, upon which dose member 2 and the drive feature 6 are permanently locked together.

In FIG. 2C, the situation after protrusion of the dose member 2 from the actuating member 3 can be seen. The dose member 2 is permanently locked the drive feature 6 by the third engagement means 18. FIG. 2C further shows the resilient element 5, being a helical spring in the expanded state of matter; the spring or, more general, resilient element 5 stays in this state of matter usually during the set and dispense action. The lateral part of the dose member 2 now makes the actuation area 20 visible for the user. The actuation area 20 comprises ribs and indentation for making the set and dispense action more comfortable for the user.

Figure 3A:
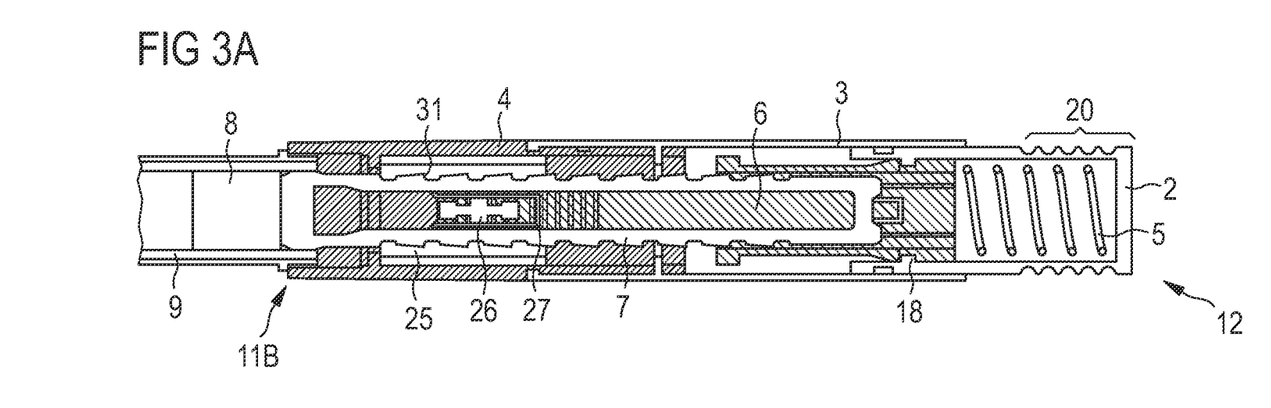
FIGS. 3A and 3B show a cross-section of the partial view of the drug delivery device of FIGS. 2A to 2C during a set and dispense action after having set the dose (FIG. 3A) and after having dispensed the dose (FIG. 3B).
Figure 3B:
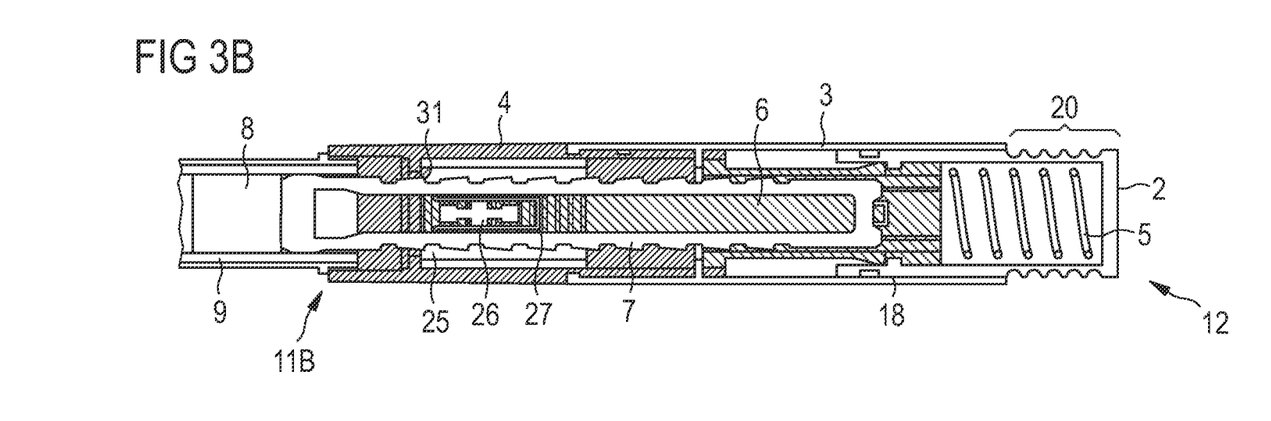

FIGS. 3A and 3B show the drug delivery device of the FIGS. 2A to 2C during the set and dispense action, i.e. in a state of matter after the priming-step has been performed. Again, the distal end of the drug delivery device has been omitted for the sake of clarity.

FIG. 3A shows the situation after the setting of the dose has been carried out. The dose member 2 has been pulled by the user in proximal direction relative to the body 4 and the driving feature 6, being fixed to the dose member 2, has been moved in proximal direction as well. By moving the drive feature 6 in proximal direction the gear 26 is also moved in proximal direction and the carrier 27, being fixed to the gear 26 latches onto the next indentation in proximal direction being arranged in the internal surface of the piston rod 7 (being not visible in FIG. 3A but visible in FIG. 1A).

FIG. 3B shows the situation after dispensing of the drug. The dose member 2 has been pushed in the distal direction thereby pushing the drive feature 6 in distal direction. This movement is translated via the gear 26 to the piston rod 7 which also moves in distal direction resulting in a displacement of the bung 8 and the delivery of a dose of medicament. A defined movement of the piston rod 7 may also be realized by the interaction of further engagement means with the indentations 31 arranged on the external surface of the piston rod 7.

Figure 4A:
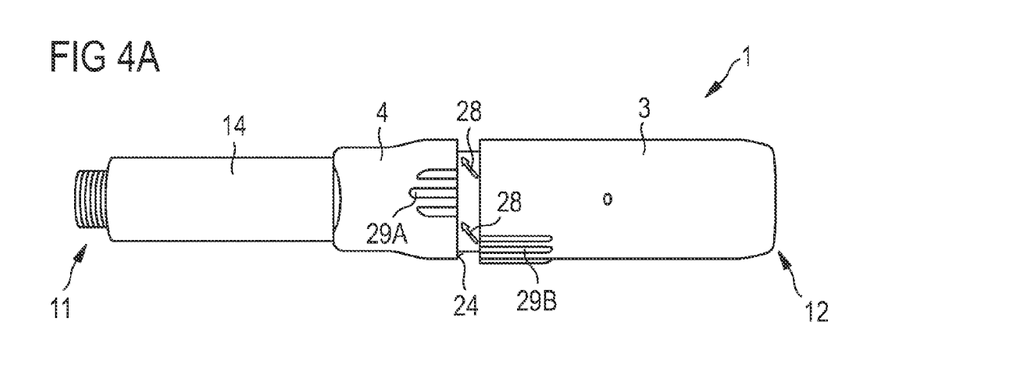
FIGS. 4A to 4C show a drug delivery device as being visible for a user in a pre-priming state (FIG. 4A), a post-priming state (FIG. 4B) and the dispense mode after having set the dose (FIG. 4C).
Figure 4B:
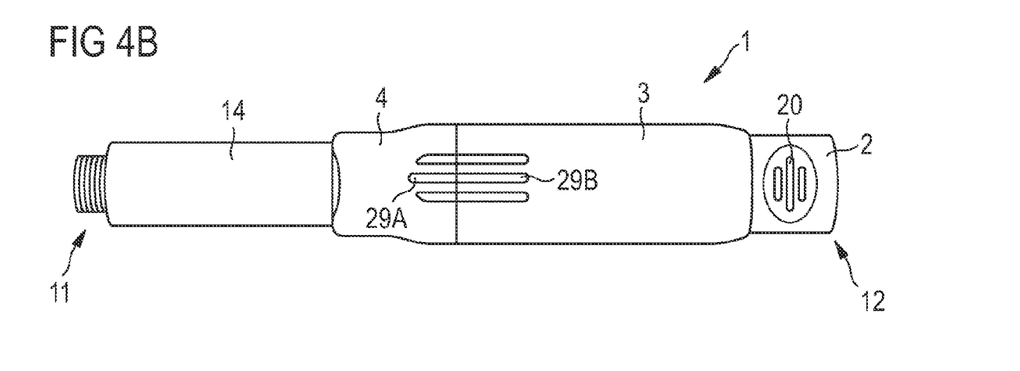
Figure 4C:
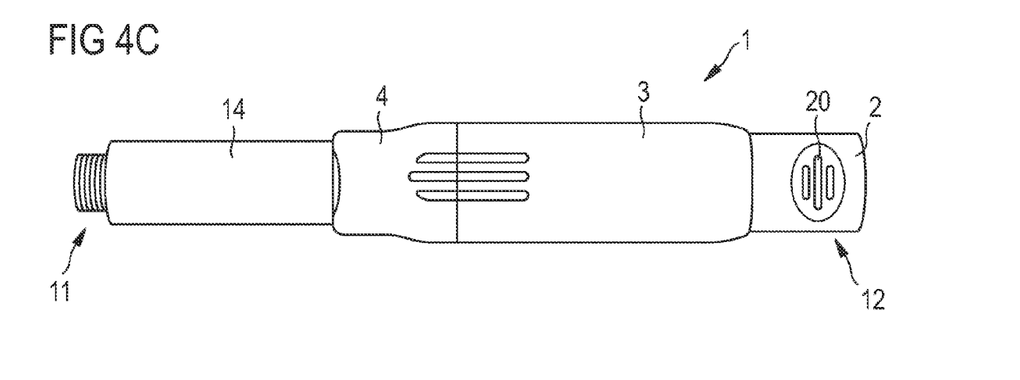

FIGS. 4A to 4C show an external view on a drug delivery device in the pre-priming state (FIG. 4A), in the post-priming state (FIG. 4B) and in the state after having set a dose (FIG. 4C).

In FIG. 4A, the housing of the drug delivery device 1, being a pen injector, can be seen. At the distal end 11 the cartridge holder 14 is arranged, which contains a cartridge containing the drug to be delivered. The cartridge contains preferably a plurality of doses of the drug. The drug preferably comprises a liquid medication, for example insulin, i.e. short-acting or long-acting insulin, GLP-1, heparin or growth hormones. The cartridge comprised in the cartridge holder 14 may comprise an outlet, which may be covered by a membrane (not explicitly shown). The drug can be dispensed from the cartridge through the outlet when the membrane is pierced. Further, the drug delivery device 1 may comprise means for securing a needle assembly (not explicitly shown), for example a screw thread, to the cartridge holder 14, particularly licated at the distal end 11 of the drug delivery device 1. The needle assembly may pierce the membrane when the drug delivery device 1 is operated.

The housing further comprises the body 4 and the actuating member 3. The proximal end of the actuating member 3 coincides with the proximal end 12 of the drug delivery device 1. Between the flange feature 24 and the distal end of the actuating member 3 the part of the body 4 being covered after having carried out the priming-step can be seen. In this part signs or inscriptions 28 are arranged on the surface in order to inform the user that the priming of the device has to be carried out though. In FIG. 4A specifically arrows are shown as signs or inscription 28. Finally, on the surface of the body 4 not being covered by the actuating member 3 after the priming-step as well as on the surface of the actuating member 3 matching symbols 29A and 29B are arranged.

FIG. 4B shows the situation after having performed the priming-step. The matching symbols 29A and 29B together show a continuous motif or structure. Preferably, these symbols may also be used as a grip for carrying out the priming-step (and therefore, preferably have a rib and indentation structure). At the proximal end 12 of the drug delivery device 1, the dose member 2 has been protruded from the actuating member 3 and the actuation area 20 is visible. Again, the actuation area comprises several ribs and indentations in order to ease the set and dispense action.

FIG. 4C shows the drug delivery device after having set the dose. The dose member 2 further protrudes from the actuating member 3 compared to the situation in FIG. 4B; the dose member 2 has been pulled axially in proximal direction by the user. The actuating member 3 is still fixed to the body 4 like in FIG. 4B as—according to this embodiment—the priming-step involves the fixing of the body 4 to the actuating member 3 in any direction of movement.

The present examples and embodiments are to be considered as illustrative and not restrictive, and the invention is not to be limited to the details given herein, but may be modified within this scope and equivalence of the attended claims.

The invention claimed is:

1. An assembly for a drug delivery device, the assembly being arranged to operate in two distinct modes, a priming mode starting from a pre-priming state and a dispense mode operating in a post-priming state, the assembly having a distal end and a proximal end, which are spaced apart in the direction of an axis, the assembly comprising
   a dose member,
   an actuating member, and
   a piston rod which is configured to act on a bung of an assembled cartridge containing the drug,
   wherein
   in the pre-priming state the actuating member is configured to be moved in a distal direction by a user such that the distal movement of the actuating member causes a movement of the dose member and wherein the movement of the dose member causes a movement of the piston rod and, wherein
   in the post-priming state the dose member is configured to be moved by a user without causing a movement of the actuating member in order to perform a set and dispense action of the drug delivery device.

2. The assembly according to claim 1, wherein in the pre-priming state, the actuating member is engaged with the dose member by first engagement means, wherein the first engagement means are arranged such that the dose member and the actuating member are disengaged by the movement of the actuating member.

3. The assembly according to claim 1, wherein in the pre-priming state the dose member is fixed to the actuating member in any direction of movement.

4. The assembly according to claim 3, wherein in the pre-priming state, the actuating member is fixed to the dose member by interconnection means, the interconnection means extending in a spatial direction being different from the direction of the axis, and wherein by movement of the actuating member a force is exerted on the interconnection means upon which the engagement of the interconnection means with at least one of the actuating member and the dose member is released and upon which the dose member and the actuating member are disengaged.

5. The assembly according to claim 1, further comprising a body, wherein the actuating member adjoins the body and wherein in the pre-priming state the actuating member is moveable with respect to the body.

6. The assembly according to claim 5, wherein in the post-priming state the actuating member is fixed to the body at least in the direction of the axis with respect to the assembly.

7. The assembly according to claim 5, wherein the actuating member is engaged to the body by second engagement means.

8. The assembly according to claim 7, wherein in the pre-priming state the second engagement means are provided to allow a rotation or a helical movement of the actuating member with respect to the body.

9. The assembly according to claim 1 further comprising a drive feature, the drive feature being provided to cause a movement of the piston rod in distal direction, wherein
   the drive feature is configured such that in the pre-priming state a movement of the actuating member causes a movement of the drive feature, and in the post-priming state the drive feature is coupled to the dose member such that a movement of the dose member causes a movement of the drive feature.

10. The assembly according to claim 1, wherein the dose member is engaged with a resilient element, the resilient element being configured to cause the dose member to protrude with respect to the actuating member when the dose member and the actuating member are disengaged during movement of the actuating member.

11. The assembly according to claim 1, wherein
   the dose member comprises an actuation area in its lateral part, the actuation area being used for the actuation of the dose member in the post-priming state in order to perform a set and dispense action,
   wherein in the pre-priming state the actuation area is at least partially covered by a component of the assembly.

12. The assembly according to claim 1, wherein the actuating member is a sleeve.

13. The assembly according to claim 1, wherein in the dispense mode the dose member is moveable in proximal direction of the axis in order to allow setting of a dose of a drug contained in a cartridge contained in the drug delivery device, and the dose member being subsequently moveable in distal direction of the axis with respect to the body in order to allow a dispense of the dose.

* * * * *